United States Patent
Koyama et al.

(10) Patent No.: US 6,491,725 B1
(45) Date of Patent: Dec. 10, 2002

(54) KEYHOLE BUTTON

(75) Inventors: Junichi Koyama, Nagano-ken; Yukio Taniguchi, Saitama-ken; Takamitsu Yoshida, Saitama-ken; Yoshiro Imamura, Saitama-ken, all of (JP)

(73) Assignee: Asahi Kogaku Kogyo Kabushiki Kaisha, Tokyo (JP)

(*) Notice: Subject to any disclaimer, the term of this patent is extended or adjusted under 35 U.S.C. 154(b) by 12 days.

(21) Appl. No.: 09/691,158

(22) Filed: Oct. 19, 2000

(30) Foreign Application Priority Data

Oct. 20, 1999 (JP) .......................................... 11-298783

(51) Int. Cl.⁷ ................................ A61F 2/44; A61F 2/36
(52) U.S. Cl. ................................ 623/17.19; 623/23.48
(58) Field of Search .......................... 623/16.11, 17.11, 623/17.15, 17.16, 17.17, 17.8, 17.19, 23.48; 606/232

(56) References Cited

U.S. PATENT DOCUMENTS

| | | | |
|---|---|---|---|
| 4,113,500 A | | 9/1978 | Ebihara et al. |
| 4,904,257 A | | 2/1990 | Mori et al. |
| 5,458,643 A | * | 10/1995 | Oka et al. ................. 623/17.16 |
| 6,146,422 A | * | 11/2000 | Lawson ................... 623/17.11 |
| 6,296,665 B1 | * | 10/2001 | Strnad et al. ............ 623/17.16 |

OTHER PUBLICATIONS

T. Yamashima, "Reconstruction of Surgical Skull Defects with Hydroxylapatite Ceramic Buttons and Granules", 1988.*

"Reconstrcution of Surgical Skull Defects with Hydroxylapatite Ceramic buttons and Granules" by T. Yamashima, puublished in 1988.

* cited by examiner

Primary Examiner—Corrine McDermott
Assistant Examiner—Hieu Phan
(74) Attorney, Agent, or Firm—Greenblum & Bernstein, P.L.C.

(57) ABSTRACT

A keyhole button used as a supplement of a keyhole portion formed on a cranium is constituted to have a brim portion having front and back surfaces, and a shaft portion integrally provided on the back surface of the brim portion. The front surface of the brim portion is convexed in a first direction, and concaved in a second direction that is perpendicular to the first direction.

8 Claims, 3 Drawing Sheets

KEYHOLE BUTTON

BACKGROUND OF THE INVENTION

The present invention relates to a keyhole button used as replenishment for a keyhole portion of a cranium formed when trepanation of the frontal or temporal bone is performed in the field of cranial nerve surgery. More particularly, the present invention relates to a keyhole button, which is superior in the adaptability to an organism, and in the stability, and does not disfigure the appearance of face after the operation is performed.

Conventionally, many craniotomy operations and closing operations have been performed in the field of cranial nerve surgery. Generally, a craniotomy operation includes following steps:

incising a head skin and exposing a cranium;

making some fossae on a cranium by a drill in accordance with a size and a region of the portion to be trepanned;

cutting between the fossae by a line saw;

taking out a bone flap; and dissecting an internal dura mater.

In this operation, a portion at which a fossa is firstly made by drilling is located near the temple, and is called a "keyhole."

The shape of the keyhole portion varies depending on the shape of the bone of individual patient and/or a doctor who performs the operation. Accordingly, it has been difficult to make a standard product of a bone substitute (which is referred to as a keyhole button). Conventionally, when the craniotomy has been performed, resin is filled into the keyhole portion as the supplemental member. However, there is a problem in adaptability to an organism and fever thereof. Recently, the keyhole buttons made of calcium phosphate compound, which has bio-compatibility, or adaptability to an organism, are used in some cases. However, such keyhole buttons have a stability problem and/or an appearance problem since the keyhole button does not match the shape around the keyhole portion.

SUMMARY OF THE INVENTION

It is therefore an object of the present invention to provide an improved keyhole button, which has high adaptability to an organism and stability, and further, with which the appearance of the face after the operation is performed is not disfigured.

For the above object, according to the present invention, there is provided a keyhole button used as a supplement of a keyhole portion formed on a cranium. The keyhole button is constituted to have a brim portion having front and back surfaces, and a shaft portion integrally provided on the back surface of said brim portion. The front surface of the brim portion is convexed in a first direction, and concaved in a second direction that is perpendicular to the first direction. Thus, the keyhole button functions as an excellent bone supplement in view of the adaptability to an organism, stability, and an appearance after the operation.

Preferably, the shaft portion is substantially cylindrical.

Further, the brim portion has a rounded-rectangular shape having longer axis and shorter axis, the longer axis extending in said first direction, the shorter axis extending in said second direction. Furthermore, the center of said shaft portion is shifted from the center of said brim portion in said first direction.

Still optionally, a peripheral portion on said front surface of said brim portion is beveled.

It is preferable that the keyhole button is made of porous calcium phosphate compound. In this case, it is preferable that the porosity of said keyhole button is 55% or less.

Further optionally, the keyhole button is formed of porous sinter material. Since the keyhole button is formed of the porous material, the brim portion can be shaped relatively easily by sintering, the thickness of the brim portion can be made relatively small.

DESCRIPTION OF THE PREFERRED EMBODIMENT

Hereinafter, a keyhole button 1 according to an embodiment of the invention will be described with reference to the accompanying drawings.

Figure 1A:
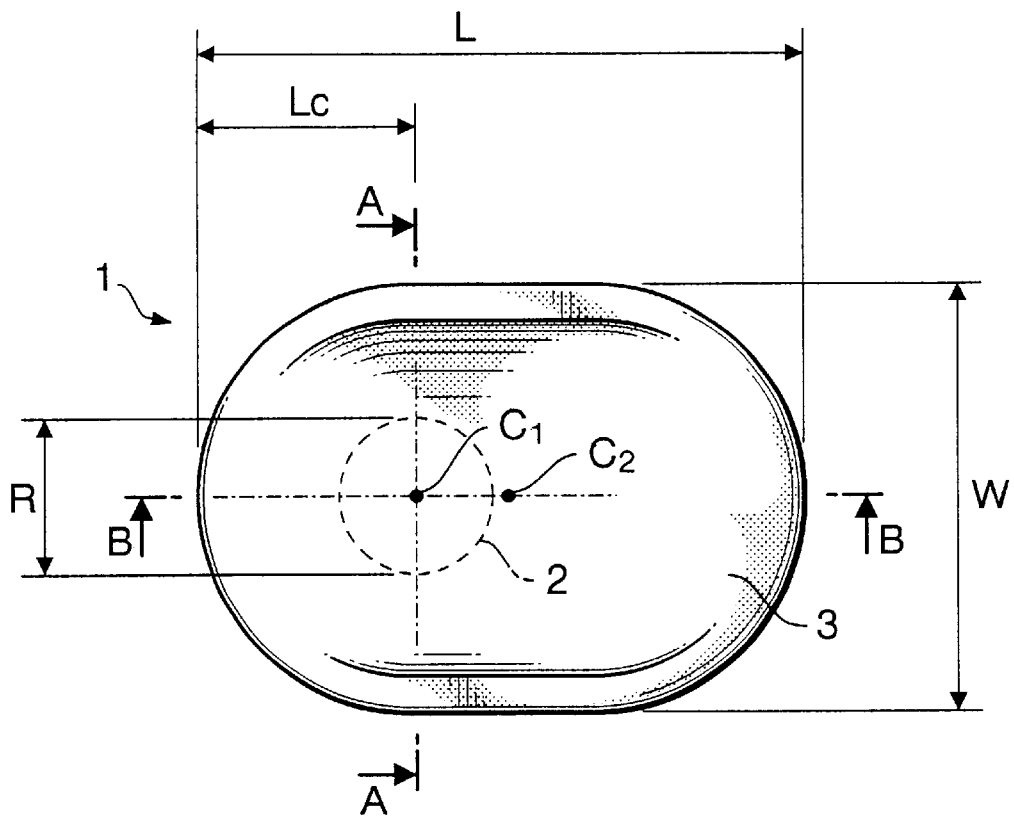
FIG. 1A is a plan view of a keyhole button according to an embodiment of the present invention.
Figure 1B:
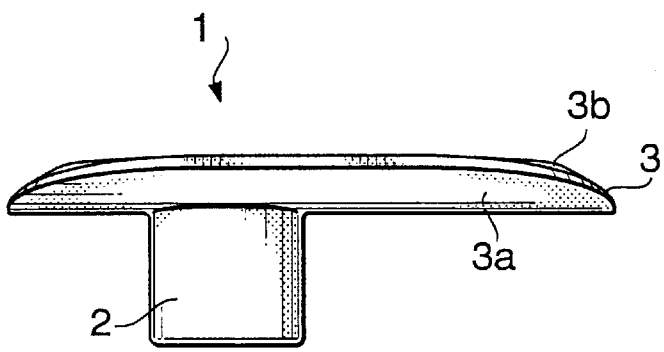
FIG. 1B is a side view of the keyhole button shown in FIG. 1A.
Figure 2A:
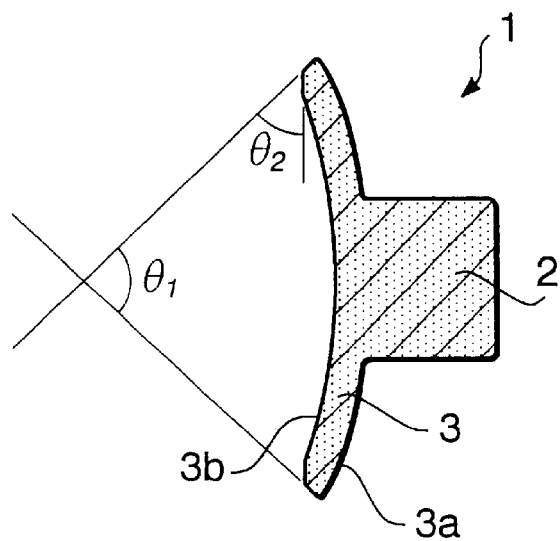
FIG. 2A is a cross-sectional view of the keyhole button taken along line A—A in FIG. 1A.
Figure 2B:
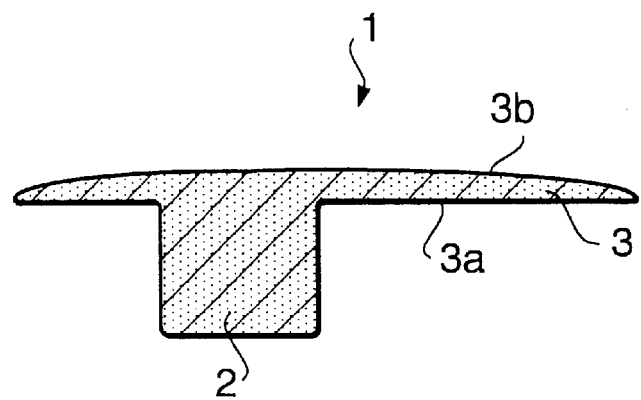
FIG. 2B is a cross-sectional view of the keyhole button taken along line B—B in FIG. 1A.
Figure 3:
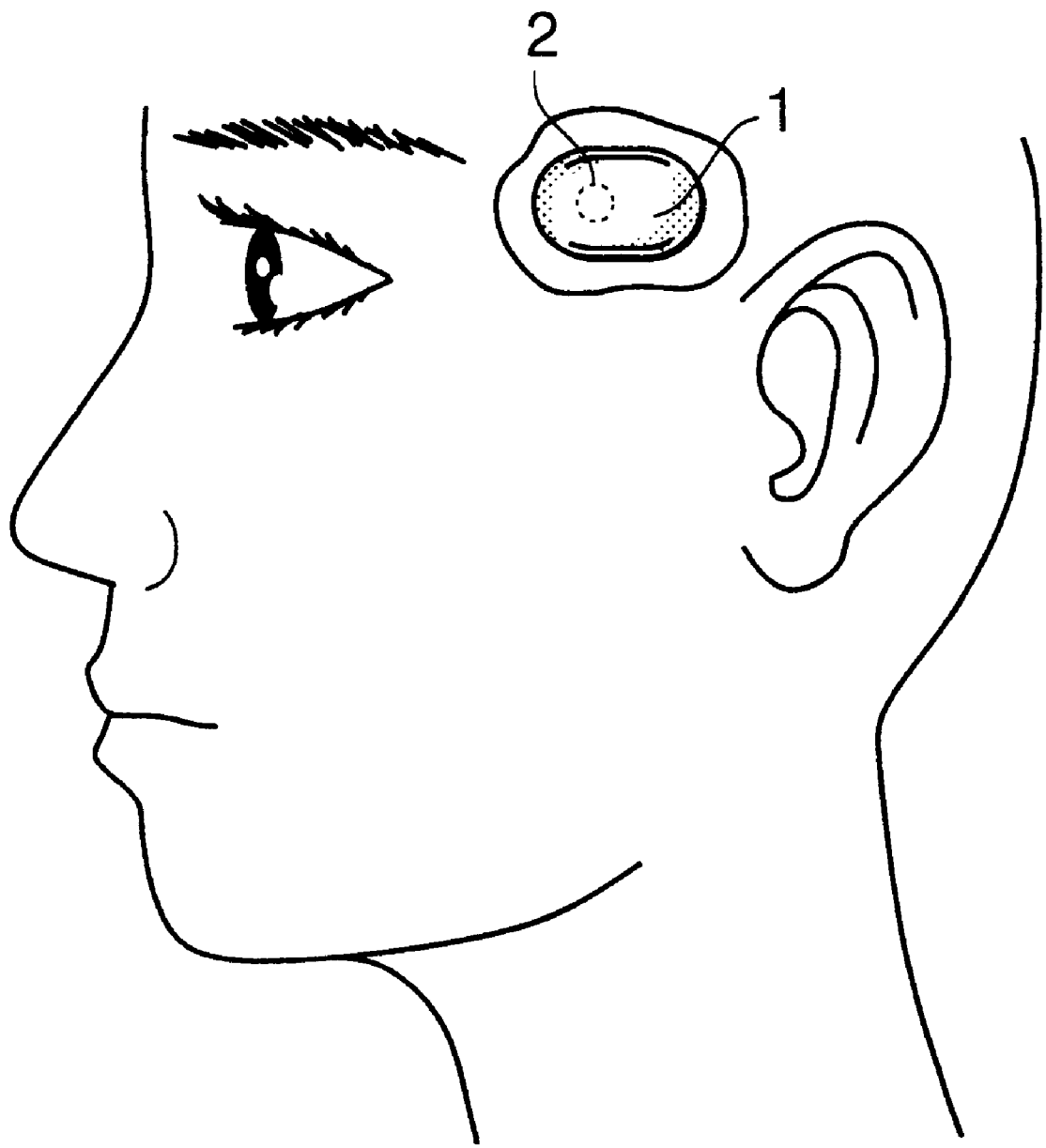
FIG. 3 is a drawing schematically illustrating an inserted keyhole button.

FIG. 1A is a plan view of the keyhole button 1 according to an embodiment of the present invention. FIG. 1B is a side view of the keyhole button 1. FIG. 2A is a cross-sectional view of the keyhole button 1 taken along line A—A in FIG. 1A, and FIG. 2B is a cross-sectional view of the keyhole button 1 taken along line B—B in FIG. 1A. FIG. 3 is a drawing schematically illustrating an inserted keyhole button 1.

As shown in FIGS. 1A–2B, the keyhole button 1 according to the embodiment has integrally formed shaft portion 2 and brim portion 3, which are formed of porous sinter. Since the keyhole button 1 is formed of the porous material, the brim portion 3, which is slightly bent, can be formed relatively easily by sintering.

Considering the strength, it is desirable that the porosity of the porous sinter is 55% or less. The porosity is defined as a ratio of the volume of pores to the volume of entire material. Preferably, the porosity is 1%–15%, and more preferably, the porosity is 10%–15%. In view of the adaptability to an organism, it is desirable that the keyhole button 1 is made of calcium phosphate compound such as monocalcium phosphate, tricalcium phosphate, hydroxyapatite $\{Ca_5(PO_4)_3OH\}$, or the like. In particular, the composition of hydroxyapatite is substantially the same as the inorganic content of an organismic bone. Accordingly, the hydroxyapatite has relatively high adaptability to an organism.

Next, the shape of the shaft portion 2 and the brim portion 3, and exemplary manufacturing methods of the keyhole button 1 will be described.

1. Brim Portion

As shown in FIG. 1A, since the brim portion 3 contacts the cranium and the muscular tissues on the upper layer of the cranium, it is desirable that the brim portion 3 has a rounded-rectangular shape. In this specification, the rounded-rectangular shape is defined as a combination of hemi-circular side portions and a rectangular portion therebetween.

In this specification, a direction along which the hemi-circular side portions and the rectangular portion are aligned is referred to as a first direction. Further, a line segment, which passes the center C1 of the rounded-rectangular shape and extends in the first direction, starting from one end to the other end of the brim portion, will be defined as a longer axis of the brim portion 3. Further, a direction, which is perpendicular to the first direction is referred to as the second direction, and a line segment extending from one end to the other end, in the second direction, of the brim portion 3 and passes the center C2 of the rounded-rectangular shape will be referred to as a shorter axis of the brim portion 3.

Because of the shape of the brim portion 3, which is symmetrical with respect to the longer axis thereof, the same keyhole button can be used for the either of right and left side keyhole portions. It is desirable that the ratio (W/L) of the length W of the shorter axis to the length L of the longer axis is, although it depends on the shape of the bone of a patient, within a range from 0.3 to 1, and more preferably from 0.4 to 0.8. Specifically, it is desirable that the brim portion 3 is formed such that the length W of the shorter axis thereof is within a range form 8 mm to 20 mm, and the length L of the longer axis is within a range of 8 mm to 30 mm, with maintaining the ratio W/L within the above range.

Besides the shape in the top view as described above, as shown in FIG. 1B, and FIGS. 2A and 2B, it is desirable that the brim portion 3 is formed such that:

(a) a lower (back) surface 3a is convexed in a direction perpendicular to the longer axis thereof (i.e., in the second direction);

(b) the lower surface 3a is represented by a substantially straight line in a cross section taken along a plane parallel to the longer axis (see FIGS. 1B and 2B);

(c) an upper (front) surface 3b is concaved in the second direction which is perpendicular to the longer axis (see FIG. 2A); and (d) the upper surface 3b is convexed in a direction (i.e., the first direction) parallel to the longer axis (see FIG. 2B).

With this shape, the brim portion 3 is well fitted to a portion where the keyhole is formed, and accordingly, both the stability and the external appearance after the operation are improved.

Generally, if the above-described shape of the brim portion 3 is formed using dense sinter material, it may be broken or cracked during sintering. According to the embodiment, since the keyhole button 1 is formed with porous material, such a bending structure can easily be formed without causing cracks.

Further generally, if the bending structure is to be formed of the porous material, the brim portion 3 tends to be made too thick in order to retain the strength. In the embodiment, the brim portion 3 is formed to have a relatively large and slightly bent shape, and further the peripheral portion is beveled so as to prevent the brim portion 3 from becoming too thick, and to retain the strength.

In FIG. 2A, a central angle $\theta 1$ for an arc of the concave surface (i. e., the upper surface 3b) or the convex surface (i.e., the lower surface 3a) is preferably within a range from 30 degrees to 160 degrees. In accordance with the central angle $\theta 1$, the length of the arc is determined. If the central angle $\theta 1$ is greater than 160 degrees, the arc may be too long. Then, it would be troublesome to process the brim portion 3 to fit onto the portion around the keyhole. Therefore, it is preferable that the central angle $\theta 1$ is 160 degrees or less. If the central angle $\theta 1$ is smaller than 30 degrees, the arc may be too short, which makes it difficult to form a sufficiently curved surface. Therefore, it is preferable that the central angle $\theta 1$ is 30 degrees or greater.

As shown in FIG. 2A, it is preferable that the peripheral portion of the brim portion 3 is beveled, and that the beveled portion is formed on a surface opposite to a surface on which the shaft 2 is provided. By forming the beveled portion, the thickness of the brim portion 3 can be decreased with maintaining sufficient strength. Further, by forming the beveled portion, an area of the brim portion 3 contacting the head skin at the keyhole portion is increased. Thus, the stability of the keyhole button 1 is improved, and further, regardless of the curving shape, the strength of the brim portion 3 can be kept sufficiently. It is preferable that substantially half a thickness is cut out for beveling. The inclination angle $\theta 2$ of the beveled portion (see FIG. 2A) is preferably within a range from 40 degrees to 70 degrees. It should be noted that the brim portion 3 is formed of the porous material, the bevel angle $\theta 2$ can be adjusted corresponding to the shape of the keyhole portion during an operation.

2. Shaft Portion

The shaft portion 2 is to be inserted into the keyhole portion. Therefore, it is desirable that the shape of the shaft portion 2 can be adjusted to correspond to the keyhole portion. Generally, the shape of the keyhole is different depending on a doctor who operates. Therefore, the shaft portion 2 should be processed so as to fit in the keyhole portion during the operation.

The conventional keyhole buttons are formed such that the shape of the shaft has a predetermined cross sectional shape such as a tear-drop shape or an elliptical shape in section. Such shafts do not always fit in keyholes, and therefore, it has been difficult to provide standard products. Further, since the shaft of the conventional keyhole button is formed of dense material, it is troublesome to process the keyhole button to have a desired shape.

According to the embodiment, however, the keyhole button is made of porous material, and therefore, it can easily be processed to have a desired shape, which fits in the keyhole. Alternatively, if the shaft portion 2 is formed to be substantially cylindrical, it may be used flexibly and widely since such a shaft may fit in almost all the deficit portions. Further, if the shaft portions are formed to have a cylindrical shape, it may be possible to provide standard products.

It should be noted that the actual length should be determined depending on the thickness of the bone of each patient. However, it is generally desirable that the length of the shaft 2 is within a range from 1 mm to 20 mm. If the length is longer than 20 mm, the tip end of the shaft 2 contacts the internal dura mater. In such a case, the brim portion 3 may be spaced from the bone, and therefore the keyhole button 1 cannot be mounted stably. Further, such a shaft 2 also causes, after the operation, a problem in an appearance such that the convex portion is formed. If the length of the shaft is shorter than 1 mm, the keyhole button 1 may not be stable. It should be noted that, since the keyhole button, according to the embodiment, is made of porous material, even if the length of the shaft is longer than necessary, the length can easily be adjusted during the operation, for example, using a luer bone forceps.

The diameter R of the shaft portion 2 also varies corresponding to the size of the keyhole portion. It is generally desirable that the ratio (R/W) of the diameter R to the width W of the shorter axis of the brim portion 3 (see FIG. 1) is within a range from 0.15 to 0.3. In other words, it is desirable that the diameter R of the shaft 2 is within a range of 1 mm to 20 mm. If the diameter R is greater than 20 mm, the brim portion 3 should also be formed large. However, such a structure is not suitable for practical use. If the diameter R is smaller than 1 mm, the keyhole button may not be stably fixed at the keyhole portion.

As shown in FIGS. 1B and 2A, the shaft 2 is provided on the convex surface 3a (i.e., the lower surface) of the brim portion 3. Since a portion at which the keyhole is slightly concaved, the convex surface 3a, on which the shaft portion 2 is provided, can be fitted thereon and fixed stably.

As shown in FIG. 3, the shaft 2 is inserted to the keyhole such that the shaft 2 is located on the front side of the temple. If the shaft 2 is provided at the center of the brim portion 3, a part of the brim portion 3 projects toward the front of the temple, and the appearance after the operation is disfigured. Therefore, it is desirable that the shaft 2 is provided at a position C1 (see FIG. 1A) that is shifted from the center C2 of the brim portion 3 along the longer axis thereof by some extent. Specifically, it is desirable that the ratio (Lc/L) of the length Lc between a closer end of the brim portion 3 and the center C1 of the shaft 2 along the longer axis to the length L between the both ends of the arc along the longer axis is within a range from 0.3 to 0.4.

3. Manufacturing Methods

According to a first example of method of manufacturing the above-described keyhole button includes steps of:

Mixing Hydroxyapatite powder calcined at 600° C.–800° C. and methylcellulose powder in a rotary mixer;

Filling in the resultant mixture powder in a rubber mold;

Applying pressure of 1 t/cm$^2$–2.5 t/cm$^2$ using a hydrostatic pressing device to obtain a dried body;

Processing the dried body into the shape shown in FIGS. 1A–2B using an NC machine with taking contraction when fired; and Firing the processed dried body for 2–5 hours, at 1100° C.–1300° C.

According to a second example of method of manufacturing the above-described keyhole button includes steps of:

Dissolving methylcellulose powder in water, and mixing the same with calcined Hydroxyapatite powder sufficiently;

Whisking the suspension (i.e., the mixture of the dissolved methylcellulose power and calcined hydroxyapatite powder) using a whisking tool;

Drying the whisked mixture in a drying machine for about one hour to form porous dried body;

Processing the dried body into the shape shown in FIGS. 1A–2B using an NC machine with taking contraction when fired; and Firing the processed dried body for 2–5 hours, at 1100° C.–1300° C.

The present disclosure relates to the subject matter contained in Japanese Patent Application No. HEI11-298783, filed on Oct. 20, 1999, which is expressly incorporated herein by reference in its entirety.

What is claim is:

1. A keyhole button used as a supplement of a keyhole portion formed on a cranium, comprising:

a brim portion having front and back surfaces; and a shaft portion integrally provided on the back surface of said brim portion, wherein the front surface of said brim portion is convexed in a first direction, and concaved in a second direction which is perpendicular to said first direction.

2. The keyhole button according to claim 1, wherein said shaft portion is substantially cylindrical.

3. The keyhole button according to claim 1, wherein said brim portion has a rounded-rectangular shape having longer axis and shorter axis, the longer axis extending in said first direction, the shorter axis extending in said second direction.

4. The keyhole button according to claim 3, wherein the center of said shaft portion is shifted from the center of said brim portion in said first direction.

5. The keyhole button according to claim 1, wherein a peripheral portion on said front surface of said brim portion is beveled.

6. The keyhole button according to claim 1, which is made of porous calcium phosphate compound.

7. The keyhole button according to claim 6, wherein the porosity of said keyhole button is 55% or less.

8. The keyhole button according to claim 1, which is formed of porous sinter material.

* * * * *